United States Patent [19]
Perkins

[11] Patent Number: 6,010,450
[45] Date of Patent: Jan. 4, 2000

[54] MEASURING ADAPTER FOR VIEWING INSTRUMENT

[75] Inventor: David G. Perkins, Syracuse, N.Y.

[73] Assignee: Welch Allyn, Inc., Skaneateles Falls, N.Y.

[21] Appl. No.: 09/106,616

[22] Filed: Jun. 29, 1998

[51] Int. Cl.[7] ........................................................ A61B 1/06
[52] U.S. Cl. ...................... 600/175; 600/117; 600/176; 600/177; 600/200; 359/799
[58] Field of Search .................... 600/117, 121, 600/127, 175, 176, 177, 182, 199, 200; 359/798, 799, 800, 801, 802, 803

[56] References Cited

U.S. PATENT DOCUMENTS

| | | | |
|---|---|---|---|
| 4,306,546 | 12/1981 | Heine et al. | 600/160 |
| 4,380,998 | 4/1983 | Kieffer, III et al. | |
| 4,660,982 | 4/1987 | Okada | 356/383 |
| 4,747,661 | 5/1988 | Ohkuwa | 385/118 |
| 4,765,313 | 8/1988 | Kumakura | 600/167 |
| 5,239,984 | 8/1993 | Cane et al. | |
| 5,363,839 | 11/1994 | Lankford. | |
| 5,379,756 | 1/1995 | Pileski et al. | |
| 5,711,756 | 1/1998 | Chikama | 600/112 |

*Primary Examiner*—Linda C. M. Dvorak
*Assistant Examiner*—Brad C. Blaise
*Attorney, Agent, or Firm*—Wall Marjama Bilinski & Burr

[57] ABSTRACT

A measuring adapter allows a viewing instrument, such as an otoscope or other imaging device, to perform surface examinations without significant modification thereto. The adapter is releasably attachable to the instrument housing and includes a distal optical element retained by an adapter housing which is suitably aligned with the distal tip opening of the diagnostic instrument, when attached thereto, for allowing a target to be viewed at a predetermined distance from the viewing system. According to a preferred embodiment, the adapter includes a baffle which causes illuminated light from the distal tip opening to obliquely impinge onto the optical element in order that a reflected image of the illumination optics is not directed to the viewing system. According to another preferred embodiment, the optical element is skewed relative to the illumination axis of the viewing instrument.

20 Claims, 6 Drawing Sheets

MEASURING ADAPTER FOR VIEWING INSTRUMENT

FIELD OF THE INVENTION

The present invention relates to the field of viewing instruments, and in particular to a measuring adapter for a medical diagnostic or other viewing instrument, such as an otoscope, that permits dermatological or other inspections to be performed in conjunction with the normal operation of the instrument.

BACKGROUND OF THE INVENTION

A number of medical diagnostic instruments are known that allow inspections of body cavities with minimal invasiveness of a patient. An otoscope, for example, is used for examining the interior of the ear canal and includes an elongated body portion and a depending handle portion. The body portion includes an distal frusto-conical insertion portion which is sized for placement within the ear canal. An imaging system, such as a rod lens assembly, located within the insertion portion focuses an optical image of a target for viewing through a proximally located eyepiece portion.

More recently, otoscopes, as well as other medical diagnostic instruments, have been configured to allow the positioning of a miniature video camera, including a solid-state imager such as a CCD, CMOS, or other similar device which converts an optical image from a focusing lens system into electrical signals for transmission. The transmitted electrical signals are then often converted into a monitor-ready video signal format (PAL, NTSC, SECAM etc.) for display on a peripheral device, such as a video monitor. To that end, instruments are also known in which the video camera can be positioned as a proximal attachment essentially replacing the eyepiece portion, such as described in U.S. Pat. No. 5,363,839 issued to Lankford, and U.S. Pat. No. 5,239,984 issued to Cane et al, among others. Alternately, a miniature video camera can be positioned in the distal end of the instrument, such as described in commonly assigned and copending U.S. patent application Ser. No. 08/818,422 to Monroe, et al., and U.S. Pat. No. 5,379,756 issued to Pileski. In each instance, the target of interest is illuminated using a plurality of optical fibers arranged or otherwise adjacent the tip opening of the distal insertion portion. The source of illumination can be a halogen lamp provided within the handle portion, such as described in U.S. Pat. No. 5,239,984, or an externally disposed light box, as is commonly known.

Another commonly known medical diagnostic instrument is a skin surface microscope (also commonly referred to as a dermatoscope) used to examine skin disorders, such as moles, warts, lesions, and the like. An increase in the incidence rate of melanomic and other skin cancers has produce a more heightened concern, thereby increasing the need for these examinations.

Typically, a skin surface microscope includes a body portion having a viewing optic having a relatively large diameter (approximately 25 cm) disposed at a distal end thereof. The distal viewing optic includes a measuring reticle to provide a frame of reference relative to the target of interest which is viewed through a proximal eyepiece portion, preferably having at least one magnifying optic. In use, the distal viewing optic is placed in direct contact with a portion of skin surface of interest, and the target is viewed through the eyepiece portion. A videoized version of this instrument is manufactured under the tradename of Video Episcope™ by Welch Allyn, Inc. Other similar instruments are manufactured by Heine Instruments, Inc.

As in the case of other diagnostic instruments, illumination is required in order to adequately view the target. Typically, skin surface microscopes include a light source, usually a halogen lamp, contained in the handle and oriented at an acute angle to effectively illuminate the viewing optic and target.

With the minimal amount of space available in a doctor's office there is a general desire to improve the general efficiency therein. Therefore, it would be desirable to allow a physician to be able to use a single diagnostic instrument interchangeably to perform several different examination procedures. There are a number of associated problems, however, which have made the notion of providing a skin surface microscopic attachment for a standard video otoscope difficult to implement. Because the illumination and viewing axes of the video otoscope are substantially collinear, a typical episcopic viewing window would invariably reflect an image of the illuminator into the image as perceived by the viewing optics. In addition, direct illumination also produces glare, from the skin and reticle, making examination ineffective, in either instance, without significant modification of the instrument.

Another problem confronted in the use of skin contacting microscopes occurs in the case of raised skin disorders, such as warts, etc. Typically, physicians use oil in conjunction with the air/skin boundary in order to eliminate surface glare and allow viewing deeper into the skin. A conventional skin contacting optical element used for measuring or observing the disorder is likely to compress the target. There are occasions, however, when the physician may desire to view the disorder in an uncompressed state.

SUMMARY OF THE INVENTION

A primary object of the present invention is to improve the state of the art of viewing instruments.

Another primary object of the present invention is to provide a viewing instrument which is capable of performing multiple forms of inspection without a significant increase in either space or cost or requiring modification of the instrument.

Another primary object of the present invention is to provide a measuring adapter suitable for an existing otoscopic device which expediently and interchangeably allows both otoscopic as well as dermatological or other surface-related examinations.

Still another primary object of the present invention is to provide a measuring adapter for an otoscope which allows examination without glare, reflection or other problems typically occurring from illumination systems used in such instruments.

Therefore, and according to a preferred aspect of the present invention, there is described a measuring adaptor for a viewing instrument, said instrument comprising:

an instrument housing including a distal tip opening;

a viewing system disposed within said housing to allow viewing of a target of interest through said distal tip opening; and means disposed within said housing for illuminating said target of interest through said distal tip opening, wherein said measuring adapter includes an adapter housing which is releasably attachable to said instrument housing and an optical element distally retained by said adapter housing, said optical element being aligned with said distal tip opening when said adapter is attached to said housing for allowing a target to be viewed using said viewing system and in which said adapter is placed in contact with a surface of said target to establish a predetermined distance between said viewing system and said target surface.

In a preferred embodiment, the optical element is a viewing window which is angled relative to parallel viewing and illumination axes of the instrument to prevent a reflected image of the illumination optics from being viewed through the viewing system. In another preferred embodiment, a light baffle redirects light away from the illumination axis to avoid specular glare. The baffle, however, does not interfere with the operation of either the viewing or illumination systems of the instrument.

According to another preferred aspect of the present invention, an otoscope is provided which is capable of performing skin surface examinations and comprises:

an instrument housing including an insertion section sized for insertion into the ear canal and having a distal tip opening;

a viewing system disposed in said housing and capable of viewing a target of interest through said distal tip opening;

illumination means for projecting light through said distal tip opening along an illumination axis; and a measuring adapter including an adapter housing which is releasably attachable to said insertion section and a distal optical element retained by said adapter housing, said distal optical element being aligned with said distal tip opening for allowing a target to be viewed when said adapter is attached to said insertion section.

An advantage of the present invention is that a single viewing instrument is provided which can be interchangeably used for different examination procedures, thereby increasing the efficacy of office practice.

Another advantage of the present invention is that an dermatological adapter for an optical or video medical viewing instrument, provides a physician or other caregiver with substantial savings in space and cost, which are typically at a premium.

Another advantage of the present invention is that the described instrument can be quickly converted to allow separate examination procedures by simply adding or removing the adapter from the instrument body.

These and other objects, features, and advantages are provided in the following Description of the Invention when should be read in conjunction with the accompanying drawings.

DETAILED DESCRIPTION OF THE INVENTION

Each of the following embodiments specifically describe an dermatological adapter as used with a videoized otoscope. It will be apparent from following discussion, however, that the described adapter can effectively be used with any imaging instrument having coaxial viewing and illumination axes, including both optical or videoized instrument versions.

Figure 1:
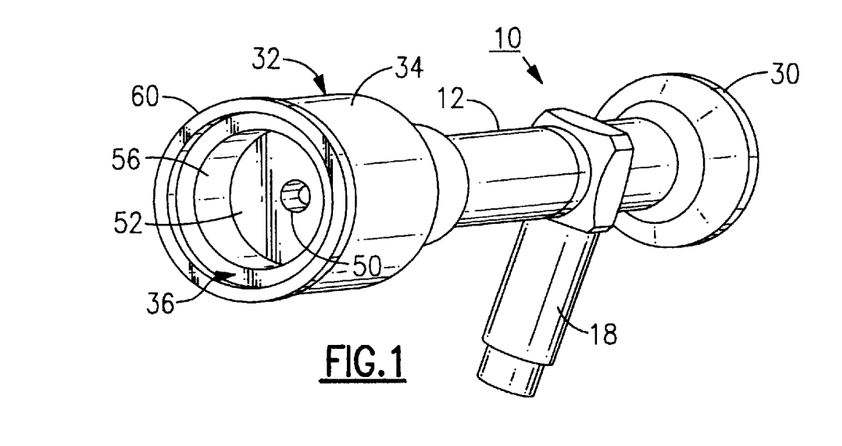
FIG. 1 is a front perspective view of a videoized medical diagnostic instrument equipped with a dermatological adapter in accordance with a first embodiment of the present invention.
Figure 2A:
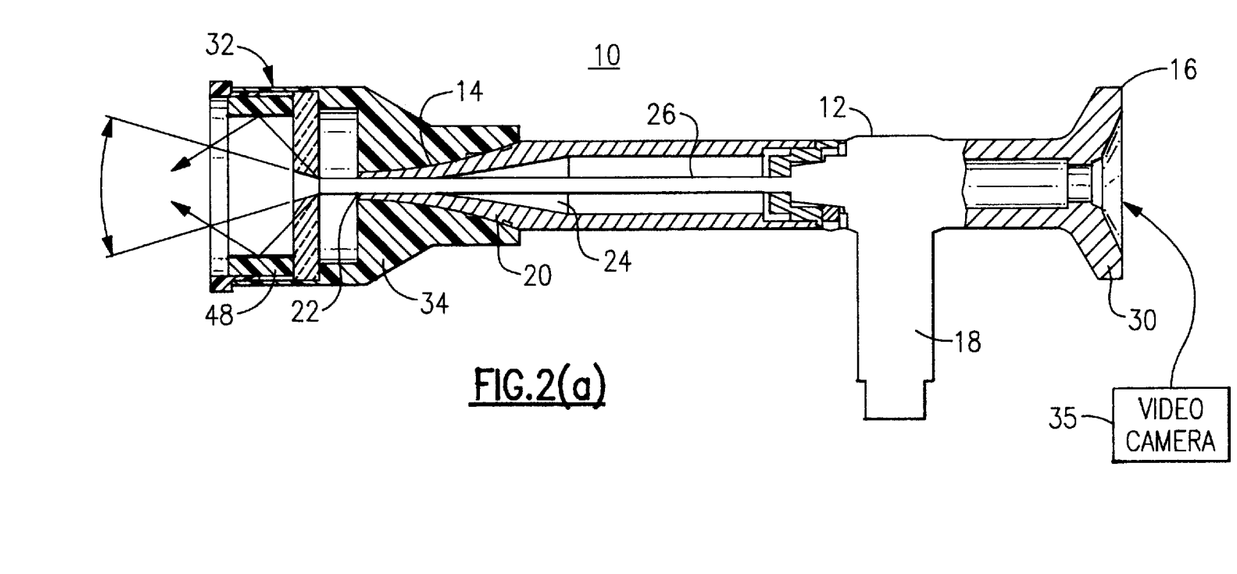
FIG. 2(a) is a sectional view of the video diagnostic instrument and adapter of FIG. 1.
Figure 2B:
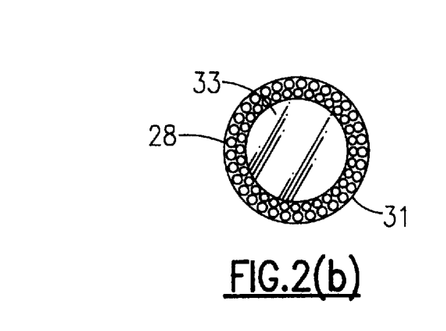
FIG. 2(b) is a partial end view of the illumination and viewing optics of the diagnostic instrument of FIGS. 1 and 2(a)
Figure 3:
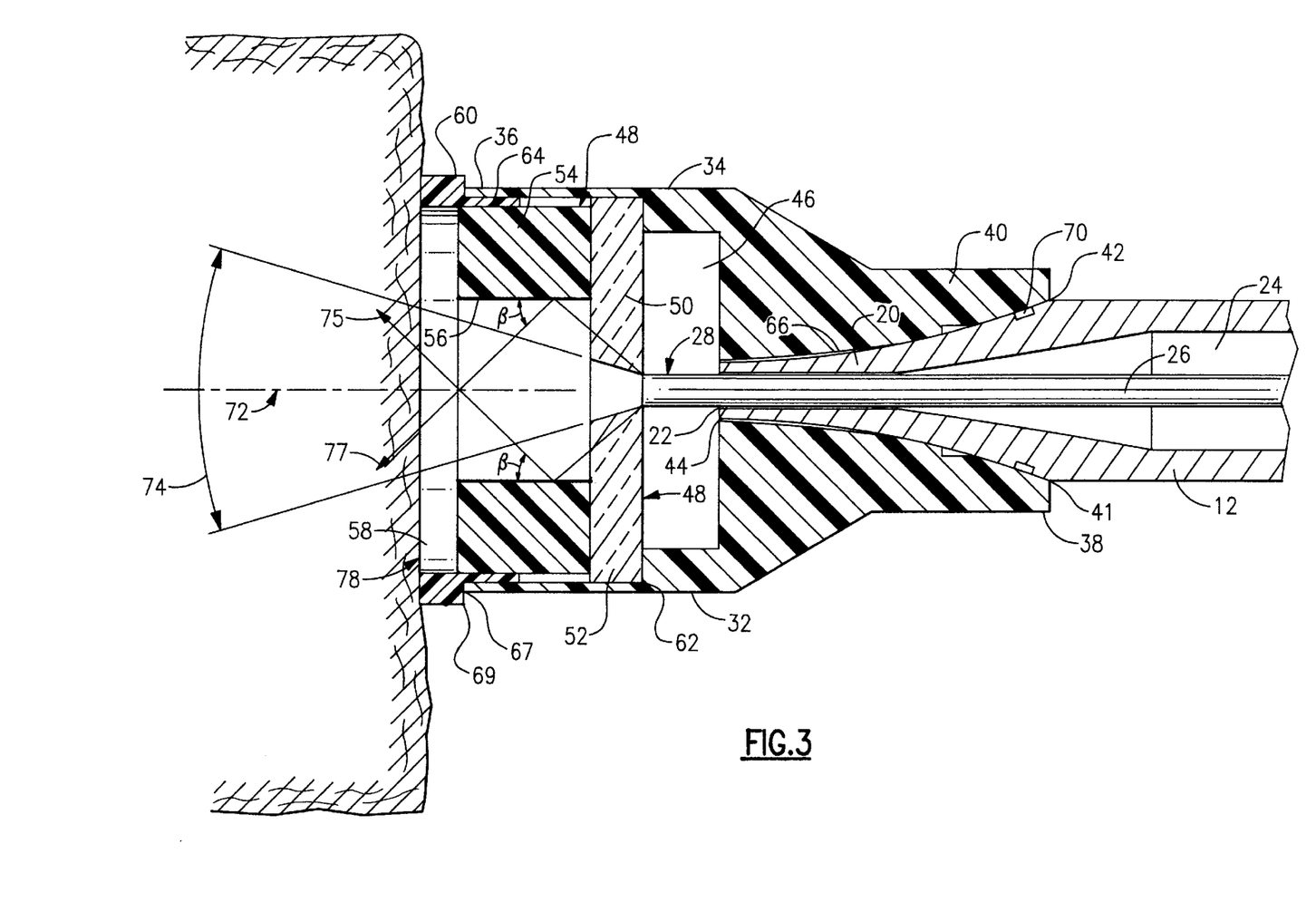
FIG. 3 is an enlarged partial sectional view of the dermatological adapter of FIG. 2.

Referring to FIGS. 1–3, a first embodiment of the present invention includes a video otoscope 10 having a body portion 12 with opposite distal and proximal ends 14, 16, as well as a handle portion 18 downwardly depending from the body portion. The distal end 14 includes a frusto-conical insertion portion 20, which is nominally sized for placement within the ear canal (not shown) to a predetermined distance. To provide a frame of reference, the diameter of a ear canal of a typical adult is between approximately 5–7 mm.

The insertion portion 20 includes a hollow interior 24 sized for receiving an elongated rod lens assembly 26 and having a distal tip opening 22. An extending rod lens end 28 protrudes outwardly from the distal tip opening 22.

Referring to FIGS. 2(a) and 2(b), the rod lens assembly 26 of the present embodiment contains both viewing and illumination optics, whereby a series of axially positioned optical rod elements 33 (partially shown in FIG. 2(b)) retained within a cylindrical rod member are surrounded therein by a bundle of optical fibers fanned out in a circumferential fashion about the optical elements. As most clearly shown in FIG. 2(b), the surrounding optical fibers include light emitting ends 31 coextensive with the outwardly protruding rod lens end 28 for projecting white light therefrom. In use, the rod lens assembly 26 gathers and directs an optical image as viewed from the extending rod end 28 through the series of axial optical elements 33 and onto a miniature video camera 35 which includes a solid-state imaging element, or other electronic imaging means in order to create a monitor-ready video signal. According to this embodiment, a proximal video camera 35, shown diagrammatically in FIG. 3, includes an electronic imager (not shown), is coupled to an eyepiece portion 30 at the proximal end 16 of the otoscope 10. The operation and workings of the rod lens assembly 26 and miniature video camera 35 are commonly known to those of skill in the art and do not form an essential part of the present invention. Each are described, for example, in U.S. Pat. No. 5,363,839, herein incorporated by reference. Therefore, further discussion is not required, except as necessary, to describe the inventive concept.

Furthermore, and as will be deduced in later discussion, the form and the locations of the optical and illumination systems of the otoscope can easily be varied when using the dermatological adapter which will now be described.

Still referring to FIGS. 1–3, the dermatological adapter 32 according to this first embodiment includes a cylindrical housing 34 having opposite distal and proximal ends 36, 38. The adapter 32 is preferably made from a moldable plastic, such as polycarbonate, though other suitable materials can easily be utilized.

Extending from the proximal end 38 of the adapter housing 34 is an engagement portion 40 having a central interior passage 41 extending into an interior cavity or chamber 46. The interior passage 41 includes a pair of through openings 42, 44 at either end, the passage having a defined inward taper and shape which generally conforms to the frusto-conical insertion portion 20 of the otoscope 10 for engagement therewith, as described in greater detail below.

Positioned within the interior cavity 46 of the dermatological adapter 32 is a light baffle 48 having a circular base plate 52 and a distally extending cylindrical barrel section 54 which is fixedly positioned within the cavity against an annular shoulder 62. When placed as described, the circular base plate 52 is positioned a predetermined distance from the distal through opening 44 of the engagement portion 40 of the adapter 32.

The circular base plate 52 includes a conically shaped center opening 50 which tapers outwardly toward the distal end 36 of the adapter 32. In addition, the base plate 52 is preferably made from a light transmissive or optically conductive material, such as Lexan or a glass having a particularized index of refraction, for reasons which are articulated below. The cylindrical barrel section 54 includes a silvered or otherwise reflective inner wall 56.

Finally, a lens holder 60 retains an optical element or window 58 which is removably attached to the distal end 36 of the adapter housing 34. The distal optical window 58 is inset within the lens holder 60 which is preferably snap-fitted to the distal end 36 of the housing 32, the lens holder having an tab portion 64 which is inserted into a circular opening 67 at the distal end 36 of the housing 32 and a corresponding annular shoulder 69 for engaging the distal edge of the adapter housing 34.

The engagement section 40 includes a circumferential slot 70 for engagement by an inner protrusion (not shown) projecting from the inner surface 66 of the passage 41. This form of attachment is as described in commonly assigned U.S. Pat. No. 4,380,998, issued to Kieffer III et al., the entire contents of which are herein incorporated by reference.

When attached, as most clearly shown in FIG. 3, the distal tip opening 22 of the frusto-conical insertion portion 20 is substantially coterminous with the distal opening 44 of the engagement section 40 of the adapter 32. This positioning allows the extending rod lens end 28 to be adjacent the center opening 50 of the base plate 52 of the baffle 48.

Referring specifically to FIG. 3, and after the dermatological adapter 32 is attached to the video otoscope 10, the conical opening 50 of the light baffle 48 is adjacent the extending rod lens end 28. The conical opening 50 is tapered to provide a field of view 74 for the viewing optics contained within the rod lens assembly 26 relative to the optical axis 72. According to this embodiment, a field of view of approximately 40 degrees is adequate, though it will be readily apparent that the opening 50 can be configured as needed for a given application.

The tapered end of the opening 50, however, is sized such that light from the illumination optics, and specifically the light emitting ends 31, FIG. 2(a), surrounding the optical elements of the rod lens assembly 26, FIG. 2(a), is not permitted to enter the opening 50, but rather must pass through the base plate 52. This light is therefore redirected due to the refractive index of the light transmissive material, which gives total internal reflection, so as to impinge upon the reflective inner walls 56 of the cylindrical barrel section 54 and then the optical window 48 at an acute angle (β) which insures that an image of the circumferential ring of light emitting ends 31, FIG. 2(b) at the rod lens end 28 is not viewed as a reflected image on the optical window 58 by the viewing optics when the window is in direct contact with the skin surface 78 of a patient as shown.

A second embodiment is now described with reference to FIGS. 4–6. For the sake of convenience, similar parts will be labeled with the same reference numerals.

Figure 4:
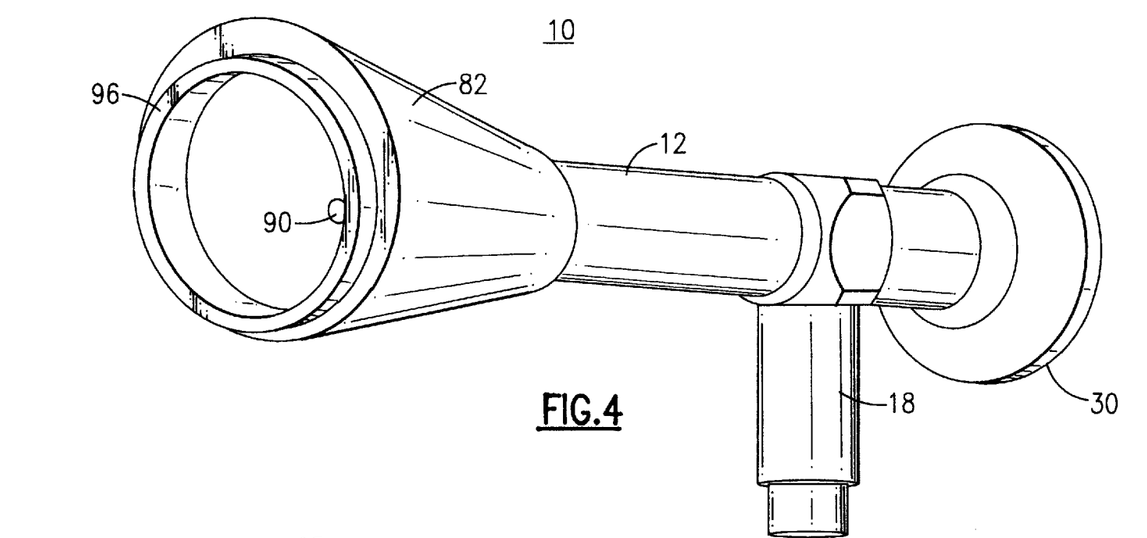
FIG. 4 is a front perspective view of a video diagnostic instrument having a dermatological adapter according to a second embodiment of the present invention.
Figure 5:
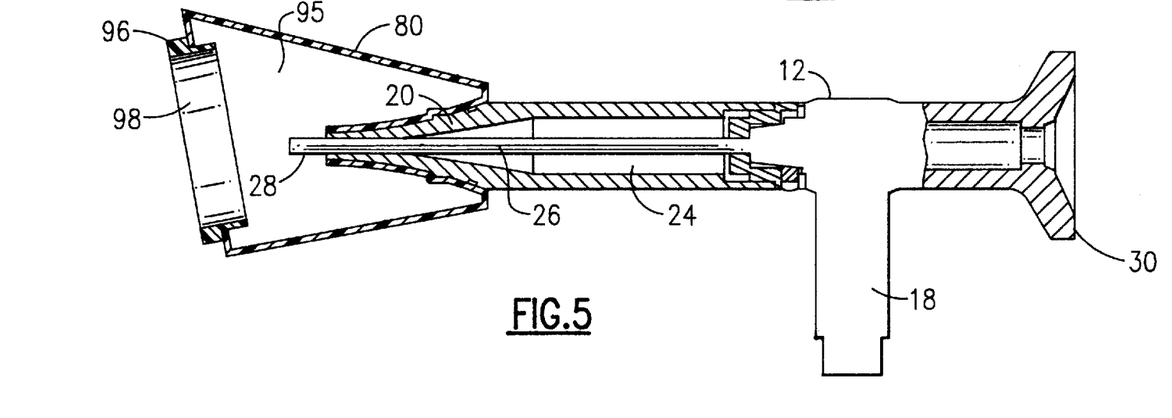
FIG. 5 is a sectional view of the video diagnostic instrument and dermatological adapter of FIG. 4.
Figure 6:
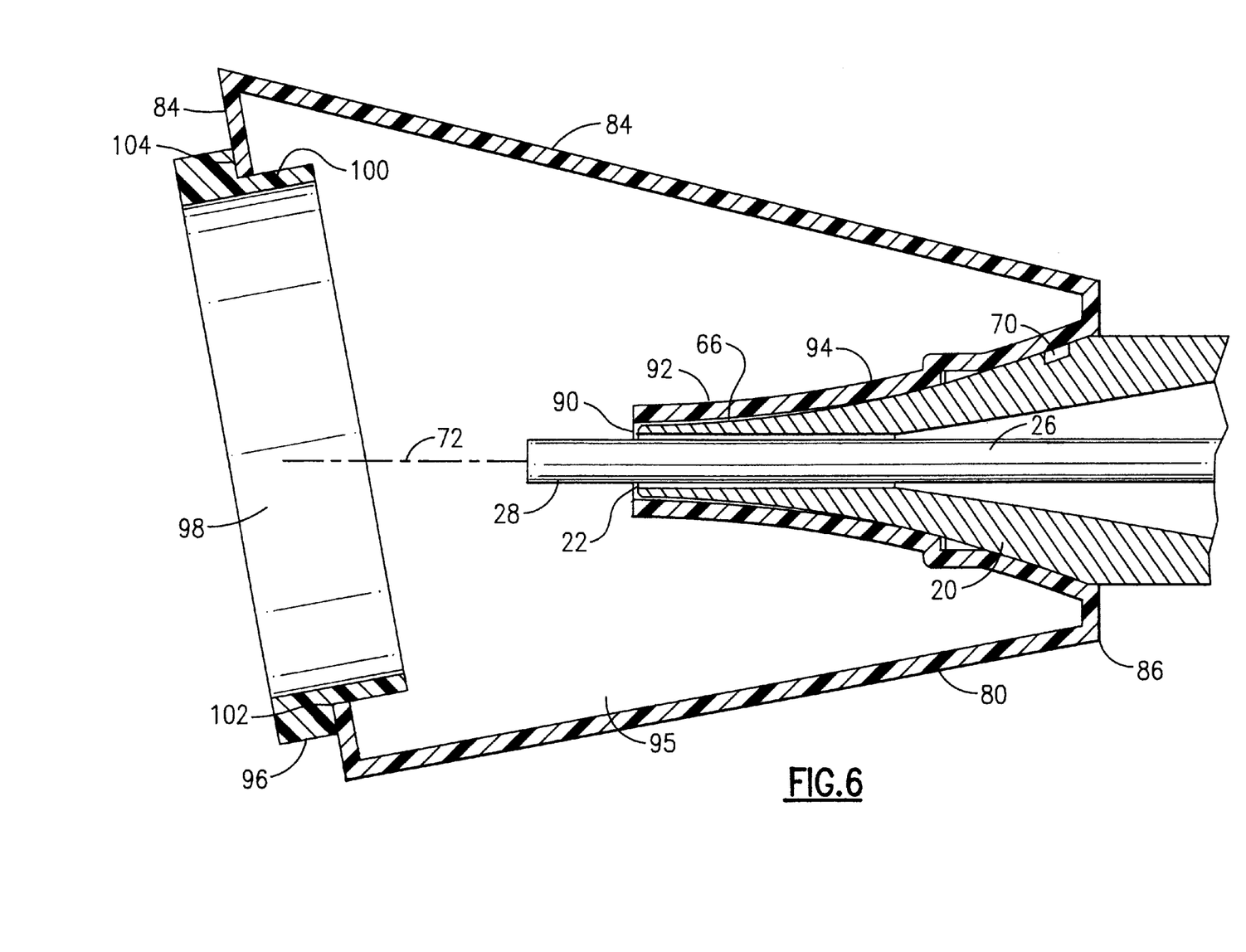
FIG. 6 is an enlarged partial sectional view of the dermatological adapter shown in FIGS. 4 and 5.

Turning to FIGS. 4–6, a video otoscope 10 is shown, similar to that previously described and having a body portion 12 and opposing distal and proximal ends 14, 16. A handle portion 18 depends downwardly from the body portion 12 therebetween.

As in the preceding, a frusto-conical insertion portion 20 extends distally from the body portion 12 nominally sized for placement within the ear canal (not shown) to a predetermined distance and having a distal tip opening 22 to allow protrusion of an extending rod lens end 28 from a rod lens assembly 26 retained within a hollow interior 24. The rod lens assembly 26 includes illumination and viewing optics generally configured as shown in the preceding FIG. 2(b) for focusing an illuminated optical image onto an electronic imager (not shown), coupled to an eyepiece portion 30 at the proximal end 16 of the otoscope 10, for conversion into a video signal which can be displayed on a video monitor (not shown) in a manner as described in U.S. Pat. No. 5,363,839, issued to Lankford, and previously incorporated above. In passing, it should be noted that other optical lens and imaging systems can be utilized. For example, the instrument could include an integral video screen in lieu of a video monitor.

The dermatological adapter 80 according to this embodiment, includes a cylindrical housing 82 made preferably from a lightweight moldable plastic and having respective distal and proximal ends 84, 86. An engagement portion 88 at the proximal end 86 of the adapter 80 is defined generally by a conical inner surface 92 so as to conform as a female connector in overlaying fashion to the frusto-conical insertion portion 20 of the otoscope 10. The engagement portion 88 includes a distal tip opening 90 interconnecting with an internal cavity 95. When attached to the otoscope 10, the tip opening 22 of the insertion portion 20 is substantially coterminous with the tip opening 90 of the engagement portion 88 and the extending rod lens end 28 protrudes into the cavity 95. In addition, the conical inner surface 92 of the engagement portion 88 includes a protrusion (not shown) for engagement with a circumferential slot 70 of the insertion portion 20, thereby retaining the dermatological adapter 80 to the otoscope 10. The described attachment is as described in the preceding embodiment and is similar to that described by U.S. Pat. No. 4,380,998 issued to Kieffer III, et al, previously incorporated by reference.

The dermatological adapter 80 according to this embodiment further includes a lens holder 96 releasably attachable to the distal end 84 having an inset skin-contacting optical window 98 preferably including a measuring reticle (not shown). The lens holder 96 includes a tab portion 100 sized to snap fit within a circular opening 102 at the distal end 84 of the housing 82. When fully inserted into the circular opening 102, a circular edge 104 of the lens holder 96 abuts the distal edge of the housing 84, providing retainment therewith. As noted, the lens holder 96 is removably attached to the dermatological adapter 80.

The distal end 84 of the adapter housing 82 according to this embodiment is skewed or angled relative to the optical axis 72 of the otoscope 10 which extends from the extending rod end 28. Providing an angular relationship between the optical window 98 and the illuminating optics prevents light from reflecting straight back from the window 98 to the protruding rod lens end 28, thereby minimizing glare and preventing a reflected image of the illumination optics from being viewed by the viewing optics of the otoscope 10. According to this embodiment, an angle of approximately 15 degrees is sufficient.

In use, the otoscope 10 can be used without the dermatological adapter 80 to perform otoscopic examinations of the ear (not shown), as is commonly known. Typically, a safety speculum (not shown) is placed over the insertion portion 20 in overlaying fashion prior to use. Use of the otoscope 10 in this manner is commonly known and requires no further discussion.

To expand the use of the otoscope 10 to allow dermatological examination, the speculum (not shown) is removed, and the dermatological adapter 80 is attached to the insertion portion 20 of the otoscope in a similar manner. The optical window 98 of the adapter 80 is then placed into direct contact with the skin surface (not shown) of the patient. As noted, no other modifications in the use of the described otoscope 10 are required. The illumination and viewing optics of the rod lens assembly 26 are used in their ordinary and intended manner, with the light from the rod lens end 28 impinging on the window 98 at a less than direct angle, but still supplying adequate illumination to allow viewing of the target (not shown) by the viewing optics for video display.

Figure 7:
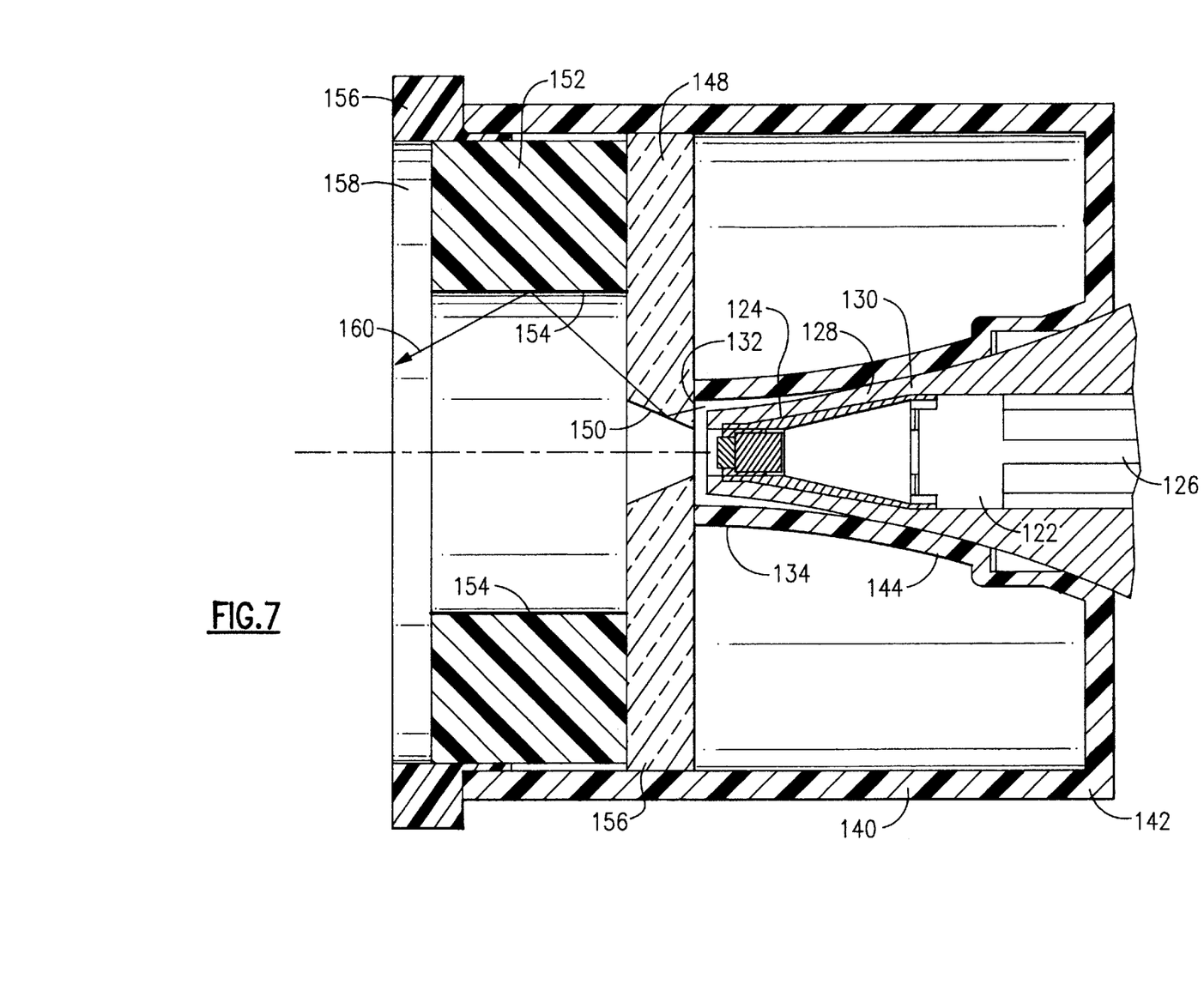
FIG. 7 is a partial sectional view of the dermatological adapter of FIGS. 1–3 used with a second form of videoized diagnostic instrument.

As noted above, the dermatological adapter according to the present invention can be used with other otoscopes having optical systems other than rod lens assemblies. Referring to FIG. 7, an dermatological adapter 140 according to a third embodiment is shown for use which utilizes an electronic imager 122 positioned in the distal end of a video otoscope 120 and, specifically within the confines of the frusto-conical insertion portion 130 which includes a distal tip opening 132. A lens cell 124 contains a number of optical elements contained in a housing 128 for focusing an optical image as viewed through the tip opening 132 onto the image plane of the imager 122. Transmission lines 126 (shown in part) then direct an electrical signal to video conditioning electronics (not shown) to provide a monitor-ready video signal. Illumination is provided by a bundle of optical fibers which extend from a source of illumination (not shown), such as a halogen lamp (not shown) contained with in the handle portion 18 or a remote light box through the body of the otoscope 120 and are fanned about the housing of the lens cell 124 in a circumferential fashion. A ring of light emitting ends 134 are arranged coterminously with the distal tip opening 132. Details relating to the workings and operation of the otoscope 120 according to this embodiment are described in greater detail in copending and commonly assigned U.S. Ser. No. 08/818,422, filed Mar. 17, 1997, by Monroe et al, the entire contents of which are herein incorporated by reference.

The instant dermatological adapter 140 is quite similar to that described in the preceding first embodiment and includes a housing 142 and an engagement portion 144 having a frusto-conical profile for conforming to the insertion portion 130 of the otoscope 120. A light baffle 146 includes a circular base plate 148 having a conically shaped opening 150 which when attached is immediately adjacent the tip opening 132 of the insertion portion 130. The baffle 146 also includes a cylindrical barrel section 152 extending distally from the base plate 148 and having a cylindrical inner wall 154 which has been treated for internal reflection.

A lens holder 156 at the distal end of the episcopic adapter 140 includes an optical window 158, preferably including a measuring reticle (not shown) which is placed in direct contact with the skin surface (not shown) of a patient.

In operation, the opening 150 within the baffle 146 is sized to provide a field of view for the viewing optics contained in the lens cell 124, but the base plate 148, preferably made from a light transmissive material reflects the light from the light emitting ends 134 to the inner walls 154 of the cylindrical portion 152 of the baffle. The light, shown as arrow 160, is then reflected from the inner wall 154 and through the optical window 158 at an acute angle.

As is readily apparent, the dermatological adapter 140 allows either otoscopic or dermatological examinations to be performed in a simple and efficient manner.

The preceding examples have all referred to a skin-contacting optical window for the presently described adapter. In nearly all instances, physicians prefer to place the optical window in direct contact with the skin surface, preferably after coating the skin surface with oil to promote an effective seal and further to reduce surface glare and allow the optics to view deeper into the skin.

Figure 8:
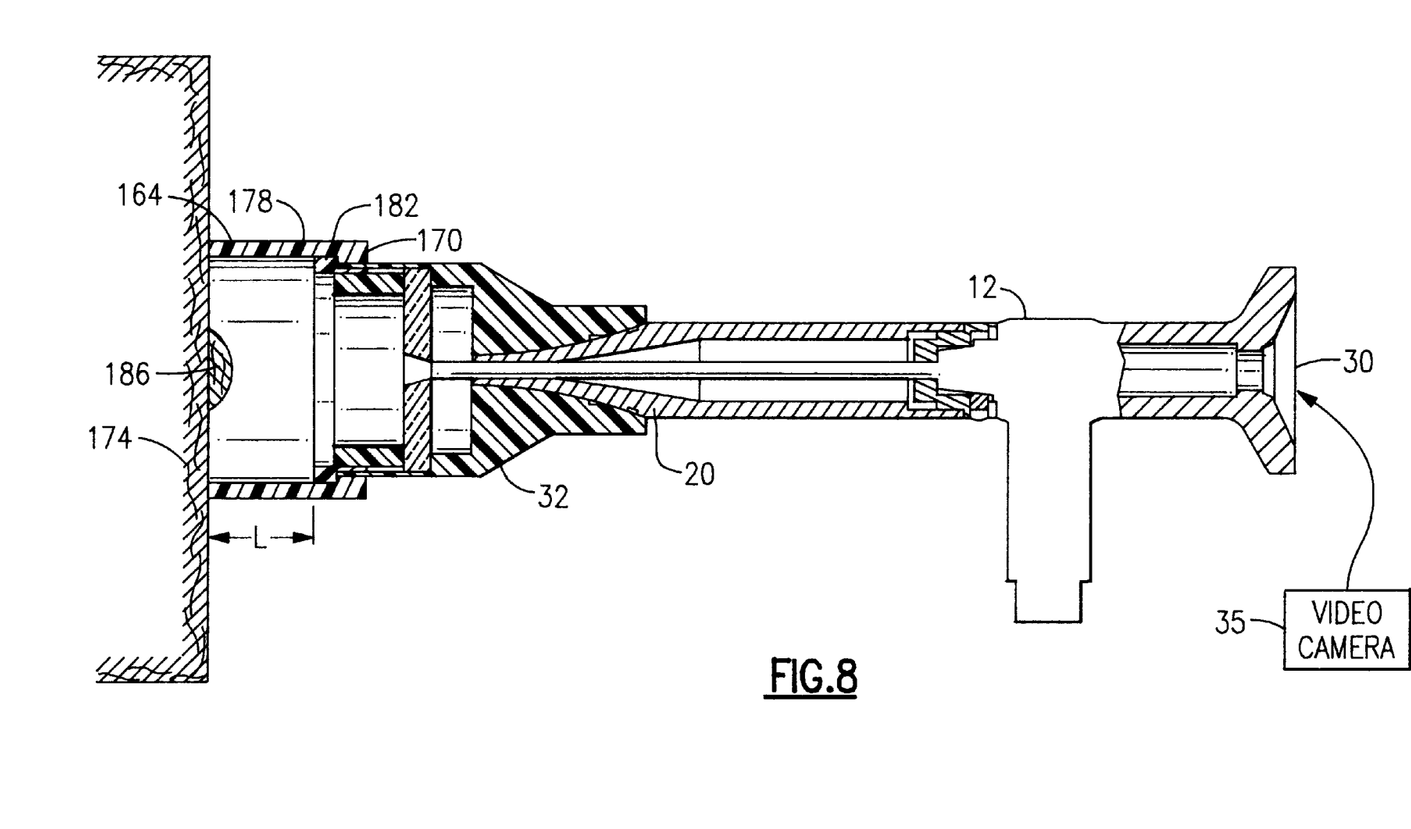
FIG. 8 is a partial sectional view of a dermatological adapter according to a third embodiment of the present invention.

An alternate embodiment is shown in FIG. 8 wherein an adaptive extending ring 164 is attachable to the lens holder so as to not to squash any large nevi 186 during viewing. According to this embodiment, the adaptive ring 164 is a uniform cylindrical section having a pair of open ends, 170, 174 the ring having a slot 182 including a shoulder 178 for engaging the distal edge of the dermatological adapter 32. The adaptive ring 164 has a length dimension -L-, as measured from the shoulder 178 to the open end 174 which is large enough to prevent the target of interest, in this case nevus 186, from being squashed during examination as shown in FIG. 8.

PARTS LIST FOR FIGS. 1–8

10 video otoscope
12 body portion
14 distal end
16 proximal end
18 handle portion
20 insertion portion
22 tip opening
24 interior
26 elongated rod lens assembly
28 extending rod lens end
30 eyepiece portion
31 light emitting ends
32 dermatological adapter
33 optical elements
34 housing
35 video camera
36 distal end
38 proximal end
40 engagement section
42 opening
44 opening
46 cavity
48 baffle
50 conical opening
52 base plate
54 cylindrical barrel portion
56 reflectorized inner side walls
58 skin contacting window
60 lens holder
62 annular shoulder 64 tab portion
66 inner surface
67 circular opening
68 protrusion
69 shoulder
70 circumferential slot
72 optical axis
74 field of view
75 arrow
77 arrow
78 skin
80 dermatological adapter
82 housing
84 distal end
86 proximal end
88 engagement section
90 distal tip opening
94 conical inner surface
95 cavity
96 lens holder
98 optical window
100 tab portion
102 circular opening
104 annular seating surface
120 otoscope
122 electronic imager
124 lens cell
126 transmission lines
130 insertion portion
132 tip opening
134 light emitting ends
140 dermatological adapter
142 housing
144 engagement portion
146 baffle
148 base plate
150 conically shaped opening
152 cylindrical barrel section
154 inner wall
156 lens holder
158 optical window
160 arrow
164 adaptive extender ring
166 attachment portion
168 recess
170 open end
172 reticle
174 open end
176 skin
178 shoulder
180 lesion
182 slot
186 target
L length dimension
β angle This invention has been described with respect to specific embodiments, though it will be readily apparent that other configurations and/or modifications can be effected within the spirit and scope of the invention. For example, the dermatological adapter can be formed integrally with a safety speculum, or may be formed as a separate component which can alternately be directly attached to the exterior of an attached safety speculum.

I claim:

1. A measuring adapter for a viewing instrument, said instrument including an instrument housing including a distal tip opening, a viewing system disposed within said housing to allow viewing of a target of interest through said distal tip opening, and means for illuminating said target of interest through said distal tip opening, and means for illuminating said target of interest through said distal tip opening, wherein said viewing system and said illuminating means include respective parallel imaging and illumination axes, said adapter including means for preventing illumination projected along said illumination axis from being reflected toward said distal tip opening along said imaging axis, said measuring adapter being releasably attachable to said instrument housing and includes at least one optical element retained by an adapter housing, said at least one optical element being aligned with said distal tip opening when said adapter is attached to said instrument housing for allowing a target to be viewed using said viewing system and in which said adapter is placed in contact with a target surface to establish a predetermined distance between said viewing system and said target.

2. The combination as recited in claim 1, wherein said illumination and imaging axes are coaxial.

3. The combination as recited in claim 1, wherein at least one optical element of said adapter is angled relative to said imaging axis to minimize specular glare.

4. The combination as recited in claim 1, including baffle means for redirecting at least a portion of illuminating light projected through said distal tip opening to cause the light to indirectly impinge upon said said at least one optical element.

5. The combination as recited in claim 4, wherein said viewing system includes at least one lens disposed adjacent said distal tip opening and said illuminating means includes light pipe means having light emitting ends arranged circumferentially about said at least one optical member.

6. The combination as recited in claim 5, wherein said viewing system includes video imaging means onto which said at least one lens focuses an optical image along said imaging axis.

7. The combination as recited in claim 6, wherein said video imaging means includes an electronic imaging sensor disposed adjacently to said distal tip opening within said instrument housing along said viewing axis.

8. The combination as recited in claim 4, wherein said baffle means includes a first light directing element disposed between said distal tip opening and said at least one optical member, said first light directing element having at least one light directing surface angled relative to said illuminating axis and having an opening aligned with said distal tip opening when said adapter is attached to said instrument housing.

9. The combination as recited in claim 8, wherein said opening of said first light directing element is sized to allow light to be received for viewing through said at least one optical element, said opening being conically shaped to define a field of view for said viewing system.

10. The combination as recited in claim 9, wherein said baffle means includes a second light directing element made from a reflective material for directing light from said first light directing element obliquely onto said optical element of said adapter.

11. The combination as recited in claim 10, wherein said second light directing element is disposed between said first light directing element and said at least one optical element of said adapter.

12. The combination as recited in claim 11, wherein said second light directing element includes a substantially cylindrical inner surface disposed between said first light directing element and said at least one optical element in which light is directed from said first light directing element onto said inner cylindrical surface so as to impinge indirectly upon said at least one optical element of said adapter.

13. The combination as recited in claim 1, wherein said adapter is a dermatological adapter having a skin-contacting viewing window having a reticle for determining the relative size of a target.

14. The combination as recited in claim 1, wherein at least one optical element of said adapter includes a measuring reticle.

15. The combination as recited in claim 14, wherein said measuring adapter includes a open-ended distal ring member having a reticle for allowing a skin surface target to be viewed without contacting said target.

16. The combination as recited in claim 15, wherein said open-ended distal ring member is releasably attachable to said adapter housing.

17. The combination as recited in claim 15, wherein said open-ended distal ring member is integral to said adapter housing.

18. The combination as recited in claim 1, including a speculum mounted in overlaying fashion over a distal portion of said instrument housing, said speculum having a distal tip speculum tip opening aligned with the distal tip opening, said adapter including means for releasably attaching to said speculum.

19. The combination as recited in claim 18, in which said speculum is integral to said adapter housing.

20. The combination as recited in claim 1, wherein said distal optical element is releasably detachable from said adapter housing.

\* \* \* \* \*